United States Patent [19]

Greikspoor et al.

[11] Patent Number: 5,027,660
[45] Date of Patent: Jul. 2, 1991

[54] SOIL PLASTIC LIMIT TESTING DEVICE

[76] Inventors: Daniel M. Greikspoor, 6513 A Woodrow, Austin, Tex. 78757; Leonard J. Bobrowski, Jr., 307 Raccoon Run, Buda, Tex. 78610

[21] Appl. No.: 589,182

[22] Filed: Sep. 27, 1990

[51] Int. Cl.⁵ ............................................. G01N 3/08
[52] U.S. Cl. ................................................. 73/818
[58] Field of Search ................ 73/818, 821, 822, 824, 73/866

[56] References Cited

U.S. PATENT DOCUMENTS 2,259,491  10/1941  Roller ................................ 73/822
3,443,423  5/1969   Lou Ma ............................. 73/821

*Primary Examiner*—Robert Raevis
*Attorney, Agent, or Firm*—Joseph F. Long

[57] ABSTRACT

This invention is a box-like device to reproducibly roll a soil sample into a ⅛ inch thread while at the same time drying the sample and comprises a flat base with ⅛" high side rails and a slideable top plate that slides on these rails. About a 2 gram soil sample moistened so that particles of the soil adhere to each other is rolled on water absorbent paper on contact surfaces of the unit and at the point that sections of the rolled thread break apart the percent water is determined and this percentage is the soil plastic limit.

5 Claims, 1 Drawing Sheet

SOIL PLASTIC LIMIT TESTING DEVICE

BACKGROUND OF THE INVENTION

In road building and foundation work, a soil plasticity index as outlined in ASTM D-4318 is quite generally used to give an indication of shrinking and swelling of the soil. Commonly, the specification for soil used for a road base includes limits on the plasticity index Also, in major foundation work a measure of the soil plasticity index is required to guide design of a foundation of soil replacement or modification.

As defined in ASTM-D4318, the soil plasticity index equals the soil liquid limit minus the soil plastic limit.

The liquid limit as defined is the percent of water in a ground well mixed soil sample that is present when a prescribed number of blows of a prescribed strength are sufficient to cause closure of a groove approximately ⅛" wide and ⅜" deep in the mixed wetted soil.

The plastic limit may be described as the percent water content in soil when a ⅛" rolled thread breaks apart when rolled.

The present ASTM-D4318 method of determination of the plastic limit is as follows:

Preparation of Test Specimen. Select a 20-g portion of soil from the material prepared for the liquid limit test, either after the second mixing before the test, or from the soil remaining after completion of the test. Reduce the water content of the soil to a consistency at which it can be rolled without sticking to the hands by spreading and mixing continuously on the glass plate. The drying process may be accelerated by exposing the soil to the air current from an electric fan, or by blotting with paper that does not add any fiber to the soil, such as hard surface paper toweling or high wet-strength filter paper.

Procedure. From the 20-g mass, select a portion of 1.5 to 2.0 g. Form the test specimen into an ellipsoidal mass. Roll this mass between the palm or fingers and the ground-glass plate with just sufficient pressure to roll the mass into a thread of uniform diameter throughout its length (Note 12). The thread shall be further deformed on each stroke so that its diameter is continuously reduced and its length extended until the diameter reaches 3.2±0.5 mm (0.125±0.020 in.), taking no more than 2 min (Note 13). The amount of hand or finger pressure required will vary greatly, according to the soil. Fragile soils of low plasticity are best rolled under the outer edge of the palm or at the base of the thumb.

NOTE 12-A normal rate of rolling of most soils should be 80 to 90 strokes per minute, counting a stroke as one complete motion of the hand forward and back to the starting position. This rate of rolling may have to be decreased for very fragile soils.

NOTE 13-A 3.2-mm (⅛-in.) diameter rod or tube is useful for frequent comparison with the soil thread to ascertain when the thread has reached the proper diameter, especially for inexperienced operators.

When the diameter of the thread becomes 3.2 mm, break the thread into several pieces. Squeeze the pieces together, knead between the thumb and first finger of each hand, reform into an ellipsoidal mass, and reroll. Continue this alternate rolling to a thread 3.2 mm in diameter, gathering together, kneading and rerolling, until the thread crumbles under the pressure required for rolling and the soil can no longer be rolled into a 3.2-mm diameter thread (See FIG. 7). It has no significance if the thread breaks into threads of shorter length. Roll each of these shorter threads to 3.2 mm in diameter. The only requirement for continuing is that they are able to be reformed into an ellipsoidal mass and rolled out again. The operator shall at no time attempt to produce failure at exactly 3.2 mm diameter by allowing the thread to reach 3.2 mm, then reducing the rate of rolling or the hand pressure, or both, while continuing the rolling without further deformation until the thread falls apart. It is permissible, however, to reduce the total amount of deformation for feebly plastic soils by making the initial diameter of the ellipsoidal mass nearer to the required 3.2-mm final diameter. If crumbling occurs when the thread has a diameter greater than 3.2 mm, this shall be considered a satisfactory end point, provided the soil has been previously rolled into a thread 3.2 mm in diameter. Crumbling of the thread will manifest itself differently with the various types of soil. Some soils fall apart in numerous small aggregations of particles, others may form an outside tubular layer that starts splitting at both ends. The splitting progresses toward the middle, and finally, the thread falls apart in many small platy particles. Fat clay soils require much pressure to deform the thread particularly as they approach the plastic limit. With these soils, the thread breaks into a series of barrel-shaped segments about 3.2 to 9.5 mm (⅛ to ⅜ in.) in length.

Gather the portions of the crumbled thread together and place in a weighed container. Immediately cover the container.

Select another 1.5 to 2.0 g portion of soil from the original 20-g specimen and repeat the operations described above until the container has at least 6 g of soil.

Repeat three more times to make another container holding at least 6 g of soil. Determine the water content, in percent, of the soil contained in the containers in accordance with Method D 2216. Make all weighings on the same balance.

NOTE 14-The intent of performing two plastic limit trials is to verify the consistency of the test results. It is acceptable practice to perform only one plastic limit trial when the consistency in the test results can be confirmed by other means.

Calculations. Compute the average of the two water contents. If the difference between the two water contents is greater than two percentage points, repeat the test. The plastic limit is the average of the two water contents.

The plastic limit testing device of the present invention comprises a device to facilitate drying while rolling a thread 3.2 mm (almost exactly ⅛" inch) in diameter until the water content is such that the thread breaks apart as prescribed in the ASTM test. The unit is meant to be used in carrying out the plastic limit test as outlined in ASTM-D4316.

Careful hand work gives results comparable to the more exact and more rapidly obtained results using the plastic limit test device of this invention.

We have searched but find only one patent, West Germany DT197808, Univ. of Stuttgart, that is aimed at soil plasticity testing. This differs quite markedly in approach and equipment used.

BRIEF SUMMARY OF THE INVENTION

This invention comprises a device to improve the accuracy and reproducibility of the soil plastic limit test as outlined in ASTM D-4318. In this test, about 20 gram of a soil sample ground and mixed with water to form a moist ball in an ellipsoid shape is placed between ⅛" high rails of a base of the test device and slideable top plate of a size to fit between and slide on these ⅛" high rails is placed over the sample. The slideable top plate is pressed down to ride on the ⅛" high rails and moved back and forth approximately 80 times a minute. In this way the moist soil sample is rolled to an ⅛" thread. In a preferred embodiment, moisture absorbent paper with grid lines about ⅛" apart aid in drying the sample while the sample is being rolled.

The sample is manually re-formed and re-rolled until the rolled thread breaks apart in pieces from ⅛" to ⅜" long. At This point, the pieces are picked up and weighed in a moist condition. When following ASTM-D4316, usually three samples will be rolled to such breakup condition and the total of the three will be weighed moist. They are then heated in an oven at 110 degrees C and cooled and weighed as prescribed in ASTM-D2216. The difference in weight s recorded as the water content and the number is used to calculate percent water which is called the plastic limit.

DETAILED DESCRIPTION OF THE INVENTION

Figure 1:
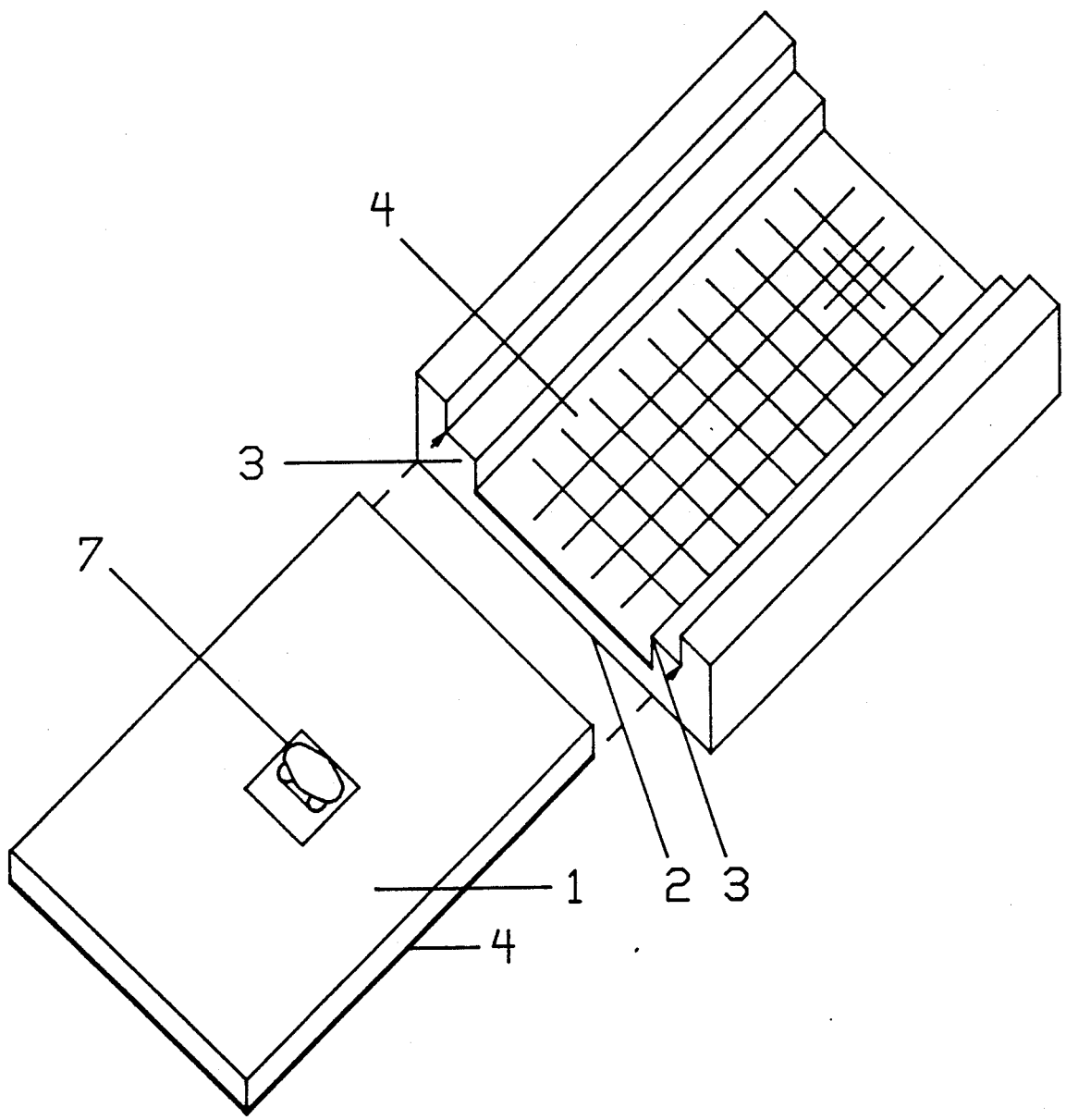
FIG. 1 shows a perspective view of the invention.

FIG. 1 shows a slideable top plate 1, preferably equipped with a knob 7 to facilitate manual sliding while putting downward pressure on the plate. In other embodiments, a mechanical set-up is used to slide this top plate back and forth a preset number of times while putting on just sufficient downward pressure to seat the slideable plate 1 on rails 3 of base plate 2. The unit may be about 4" wide and 12" long but larger sizes would work equally well. Note that multiple samples could be run on a 4" by 8" unit. Since the test requires rolling 'til the thread fractures both the underside of the top slideable plate 1 and area between the rails 3 may be covered with a water absorbent paper. The absorbent paper may have lines approximately ⅛" apart in order to facilitate measuring pieces of the rolled thread as it breaks apart. The water absorbent paper 4 is, in a preferred embodiment, held with a releaseable adhesive. In other embodiments, the water absorbent paper 4 may be fastened to slideable top 1 and base 2 with adhesive tape.

We claim:
1. A soil plastic limit testing device comprising:
  (a) a slideable top plate;
  (b) a base with dual tracks to allow said slideable top plate to move exactly ⅛" above a rolling surface of said base;
  (c) an absorbent paper releaseably held in said base and covering said rolling surface whereby the device is used in determination of the plastic limit of soil.
2. A soil plastic limit testing device as in claim 1 wherein a bottom side of said slideable top plate is also covered with said absorbent paper.
3. A soil plastic limit testing device as in claim 1 wherein said absorbent paper releaseably held in said base is marked with grid lines approximately ⅛" apart.
4. A soil plastic limit testing device as in claim 3 wherein said slideable top plate is also equipped with a knob to facilitate manual motion of said slideable top plate.
5. A soil plastic limit testing device comprising:
  (a) flat rectangular base with an L shaped track on each longer side of said flat rectangular base; said L shaped track being sized to have a surface ⅛ inch above said flat rectangular base.
  (b) a slideable top plate sized to slide within said L shaped tracks of said flat rectangular base with ⅛ inch clearance from a surface of said flat rectangular base whereby the device is used in determination of the plastic limit of soil.

* * * * *